United States Patent
Banowski et al.

(10) Patent No.: US 9,320,922 B2
(45) Date of Patent: *Apr. 26, 2016

(54) TRANSPARENT ANTIPERSPIRANT GELS

(75) Inventors: Bernhard Banowski, Düsseldorf (DE); Marcus Claas, Hilden (DE); Nadine Buse, Hilden (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 375 days.

This patent is subject to a terminal disclaimer.

(21) Appl. No.: 12/823,272

(22) Filed: Jun. 25, 2010

(65) Prior Publication Data

US 2010/0260699 A1  Oct. 14, 2010

Related U.S. Application Data

(63) Continuation of application No. PCT/EP2008/068194, filed on Dec. 22, 2008.

(30) Foreign Application Priority Data

Dec. 28, 2007  (DE) .................. 10 2007 063 351

(51) Int. Cl.
*A61K 8/28* (2006.01)
*A61Q 15/00* (2006.01)
*A61K 8/06* (2006.01)
*A61K 8/34* (2006.01)
*A61K 8/37* (2006.01)
*A61K 8/39* (2006.01)
*A61K 8/49* (2006.01)
*A61K 8/58* (2006.01)
*A61K 8/86* (2006.01)
*A61K 8/894* (2006.01)

(52) U.S. Cl.
CPC . *A61Q 15/00* (2013.01); *A61K 8/06* (2013.01); *A61K 8/064* (2013.01); *A61K 8/345* (2013.01); *A61K 8/37* (2013.01); *A61K 8/39* (2013.01); *A61K 8/4973* (2013.01); *A61K 8/585* (2013.01); *A61K 8/86* (2013.01); *A61K 8/894* (2013.01); *A61K 2800/262* (2013.01)

(58) Field of Classification Search
USPC ........................................................ 424/66
See application file for complete search history.

(56) References Cited

U.S. PATENT DOCUMENTS

| | | | |
|---|---|---|---|
| 6,007,799 A * | 12/1999 | Lee et al. | 424/65 |
| 6,482,418 B1 | 11/2002 | Loehl et al. | |
| 2004/0241196 A1* | 12/2004 | Popoff | 424/401 |
| 2006/0029624 A1* | 2/2006 | Banowski et al. | 424/401 |

FOREIGN PATENT DOCUMENTS

| | | | |
|---|---|---|---|
| WO | 9205767 A1 | | 4/1992 |
| WO | 9606594 A1 | | 3/1996 |
| WO | 9817238 A1 | | 4/1998 |
| WO | 0067888 A1 | | 11/2000 |
| WO | WO2005/063189 | * | 7/2005 |
| WO | WO 2005063189 | * | 7/2005 |

OTHER PUBLICATIONS

CETIOL® CC. Carechemicals, Retrieved from http://www.cospha.ro/dbimg/Cetioll%20CC on Dec. 21, 2010.

* cited by examiner

*Primary Examiner* — Snigdha Maewall
(74) *Attorney, Agent, or Firm* — P. Scott Smith

(57) ABSTRACT

Transparent antiperspirant compositions in the form of a water-in-oil emulsion containing a balanced mixture of selected oil components and emulsifiers, thereby improving the antiperspirant effect of the compositions.

4 Claims, No Drawings

TRANSPARENT ANTIPERSPIRANT GELS

CROSS REFERENCE TO RELATED APPLICATIONS

The present application is a continuation of International Application No. PCT/EP2008/068194 filed 22 Dec. 2008, which claims priority to German Patent Application No. 10 2007 063 351.5 filed 28 Dec. 2007.

The present Application is directed towards transparent perspiration-inhibiting compositions in the form of a water-in-oil emulsion containing a balanced mixture of selected oil components and emulsifiers in order to improve the perspiration-inhibiting effect.

Perspiration-inhibiting compositions in the form of water-in-oil emulsions are known in the art. For example, International Publication No. WO 92/05767 A1 discloses transparent perspiration-inhibiting gels in the form of a water-in-oil ("W/O") emulsion based on cyclomethicones and emulsifying ethylene oxide/propylene oxide-substituted polydimethylsiloxanes. WO 96/06594 A1 discloses transparent perspiration-inhibiting water-in-oil compositions containing volatile silicone oils and/or volatile hydrocarbon oils and the silicone-free water-in-oil emulsifiers Laureth-1 or Laureth-4. WO 98/17238 A1 discloses perspiration-inhibiting sticks in the form of a water-in-oil emulsion based on silicone-free water-in-oil emulsifiers terminally disubstituted with alkyl residues, without addressing the problem of transparency. WO 00/67888 A1 discloses low-viscosity W/O emulsions having a viscosity of no more than 5000 mPas, at least 75 wt % water phase, at most 20 wt % lipids, emulsifiers, and further lipophilic constituents wherein the oil phase has a total polarity from 20 to 30 mN/m and is free of silicones, stabilized by means of silicone-free water-in-oil emulsifiers terminally disubstituted with alkyl residues. However, this document also does not address the problem of transparency.

Transparent gels in the form of water-in-oil emulsions are very popular among consumers. Known propellant-free W/O gels based on cyclomethicones produce a fresh and care-providing feel when applied onto the skin. At the same time, they exhibit no residues directly after application. This (at first) largely residue-free application, greatly appreciated by consumers, is made visible to them due to the transparency of the composition.

For optimum transparency, the refractive index of the oil phase and water phase must be matched to one another within approximately 0.001, or even better, preferably within approximately 0.0004. If a constituent resulting in a relatively high refractive index for the aqueous phase is stipulated, for example, the effective perspiration-inhibiting aluminum-zirconium compounds, the selection of the other constituents is limited.

One problem with known gels is their high cyclomethicone content. Among commercially available cyclomethicones, a distinction is made among cyclotetrasiloxane, cyclopentasiloxane, and cyclohexasiloxane. Cyclotetrasiloxane, having an unusually high melting point of −11° C., can cause problems in shelf stability at the higher utilization quantities that are typical for a water-in-oil emulsion gel. Further, use of cyclotetrasiloxane is largely falling out of favor nowadays for environmental reasons. Typical commercial cyclomethicone products are largely free of cyclotetrasiloxane. However, even trace amounts of cyclotetrasiloxane result in cyclomethicones being a problematic raw material. On the other hand, cyclomethicones exhibit outstanding utilization properties, making them extremely difficult to replace. Cyclomethicones are relatively volatile oil components. They are therefore popular for use in cosmetics, in particular in antiperspirants, because they help solve the problem of clothing stains. Still, antiperspirants having too high a proportion of volatile cyclomethicones form white residues on the skin after drying (i.e., not until some time after application), which adhere poorly to the skin and can drip down. This is perceived by many consumers as unpleasant.

The present application therefore provides transparent perspiration-inhibiting compositions in the form of a water-in-oil emulsion that are partly or entirely free of cyclomethicones.

The present application further provides transparent perspiration-inhibiting compositions in the form of a water-in-oil emulsion having a high concentration of dispersed aqueous phase, preferably at least 75 wt %. Because commercially available perspiration-inhibiting active substances are typically water-soluble, they are present in the aqueous phase. Therefore, rapid release of the active substance is improved by a high concentration of aqueous phase.

The present Application also provides for transparent perspiration-inhibiting compositions in the form of a water-in-oil emulsion having a gel-like consistency of medium to high viscosity, which can be applied by roll-on applicator or stick-like sleeve.

The present Application provides for transparent perspiration-inhibiting compositions in the form of a water-in-oil emulsion that are partly or entirely free of cyclomethicones and exhibit good release of the perspiration-inhibiting active substance.

The present Application likewise provides for transparent perspiration-inhibiting compositions in the form of a water-in-oil emulsion that are partly or entirely free of cyclomethicones and have sufficient shelf stability.

The present Application even provides for transparent perspiration-inhibiting compositions in the form of a water-in-oil emulsion that are partly or entirely free of cyclomethicones and have sufficient shelf stability, and exhibit good release of the perspiration-inhibiting active substance.

It has been found, surprisingly, that compositions comprising 10 to 20 wt % of an external oil phase containing at least one symmetrical, asymmetrical, or cyclic ester of carbonic acid with linear or branched C6 to C22 alkanols, at least one addition product of 1 to 14 propylene oxide units with univalent or polyvalent $C_{3-16}$ alkanols, and 0 to 3 wt % cyclomethicone, 75 to 90 wt % dispersed aqueous phase having at least one perspiration-inhibiting active substance chosen from aluminum-zirconium compounds, and at least one compound chosen from water-soluble polyvalent $C_2$ to $C_9$ alkanols having 2 to 6 hydroxyl groups and water-soluble polyethylene glycols having 3 to 20 ethylene oxide units, at least one silicone-based water-in-oil emulsifier having at least one alkyl substituent R having 4 to 20 carbon atoms, at least one polyethylene glycol ether of a linear or branched C12 to C22 alkanol with 20 to 150 ethylene oxide units, and no silicone-free water-in-oil emulsifier, all wt % referring to total weight of the emulsion, provide the stated compositions in outstanding fashion.

Accordingly, the present Application is directed towards transparent perspiration-inhibiting compositions in the form of a water-in-oil emulsion, the emulsion having (a) a 10-20 wt % external oil phase containing i) at least one symmetrical, asymmetrical, or cyclic ester of carbonic acid with linear or branched C6 to C22 alkanols, ii) at least one addition product of 1 to 14 propylene oxide units with univalent or polyvalent $C_{3-16}$ alkanols, and iii) 0 to at most 3 wt % cyclomethicone, (b) a 75-90 wt % dispersed aqueous phase having i) at least one perspiration-inhibiting active substance chosen from aluminum-zirconium compounds, and ii) at least one compound chosen from water-soluble polyvalent $C_2$ to $C_9$ alkanols having 2 to 6 hydroxyl groups and water-soluble polyethylene glycols having 3 to 20 ethylene oxide units, (c) at least one silicone-based water-in-oil emulsifier having at least one alkyl substituent R having 4 to 20 carbon atoms, (d) at least one polyethylene glycol ether of a linear or branched C12 to C22 alkanol with 20 to 150 ethylene oxide units, and (e) no silicone-free water-in-oil emulsifier. All of wt % refer to, in this context, total weight of the emulsion.

The present Application further provides a non-therapeutic, cosmetic method for reducing perspiration, wherein a composition according to the present invention is applied onto the skin, preferably onto the skin in the underarm area.

Compositions according to the present invention contain 10 to 20 wt % of an external oil phase; with the oil phase content being preferably 12 to 18 wt %, particularly preferably 14 to 16 wt %, based on total weight of the emulsion. The silicone-based water-in-oil emulsifier (and if applicable, further emulsifying constituents) are not considered to be oil phase for purposes of this application. Lipophilic constituents that under standard conditions are not liquid ("oil") but instead are present in solid form (e.g., waxes) are considered to be oil phase for purposes of this application. Perfume oils are considered to be oil phase for purposes of this application. Ethanol that may optionally be present, as well as polyvalent $C_2$ to $C_9$ alkanols having 2 to 6 hydroxyl groups and water-soluble polyethylene glycols having 3 to 20 ethylene oxide units, are considered for purposes of this application to not be oil phase but water phase, even if they exhibit oil-soluble properties at least in part.

"Standard conditions", for purposes of this application, refer to a temperature of 20° C. and a pressure of 1013.25 mbar. Melting point indications refer to a pressure of 1013.25 mbar.

The oil phase can contain a combination of at least one symmetrical, asymmetrical, or cyclic ester of carbonic acid with linear or branched $C_6$ to $C_{22}$ alkanols, and at least one addition product of 1 to 14 propylene oxide units with univalent or polyvalent $C_{3-16}$ alkanols.

It has been surprisingly found that this combination of oil components represents an outstanding replacement for the cyclomethicone component in known perspiration-inhibiting W/O emulsions. These oil combinations surprisingly assist active-substance release of the perspiration-inhibiting active substance. These oils furthermore offer a pleasant skin feel similar to that of cyclomethicone. Highly transparent W/O emulsions can furthermore be manufactured very effectively using these oils, because of their refractive indices.

Preferred oil components representing symmetrical, asymmetrical, or cyclic esters of carbonic acid with linear or branched $C_6$ to $C_{22}$ alkanols include di-n-hexyl carbonate, di-n-heptyl carbonate, di-n-octyl carbonate (obtainable under the INCI name Dicaprylyl Carbonate, for example, as the commercial product Cetiol® CC of Cognis), di-2-ethylhexyl carbonate (obtainable under the INCI name Diethylhexyl Carbonate, for example, as the commercial product Tegosoft® DEC of Degussa-Evonik), di-n-nonyl carbonate, di-n-decyl carbonate, di-n-lauryl carbonate, di-n-myristyl carbonate, di-n-cetyl carbonate, di-isocetyl carbonate, di-n-stearyl carbonate, di-isostearyl carbonate, di-arachyl carbonate, and di-behenyl carbonate as symmetrically substituted carbonates, as well as asymmetrically substituted carbonates such as n-hexyl-n-octyl carbonate, n-hexyl-2-ethylhexyl carbonate, and n-octyl-n-decyl carbonate. Cyclic esters of carbonic acid are obtainable by transesterifying dimethyl carbonate or diethyl carbonate with divalent or polyvalent alkanols. Di-n-octyl carbonate, which has a refractive index $n_D$ (at 21° C.) of 1.435 to 1.436, as well as di-2-ethylhexyl carbonate, are preferred. They are preferably contained in a quantity of from 8 to 18 wt %, more preferably 10 to 16 wt %, most preferably 12 to 14 wt %, based on total emulsion.

Preferred oil components representing addition products of 1 to 14 propylene oxide units with univalent or polyvalent $C_{3-16}$ alkanols are chosen from addition products of 1 to 14 propylene oxide units with univalent or polyvalent $C_{3-16}$ alkanols, particularly with n-butanol-1, n-pentanol-1, n-hexanol-1, n-heptanol-1, n-octanol-1, n-decanol-1, n-decane-1, 10-diol, lauryl alcohol, myristyl alcohol, and cetyl alcohol. PPG-2 myristyl ether, PPG-3 myristyl ether (Witconol® APM), PPG-4 myristyl ether, PPG-5 myristyl ether, PPG-2 lauryl ether, PPG-3 lauryl ether, PPG-4 lauryl ether, PPG-5 lauryl ether, PPG-6 lauryl ether, PPG-2 decyl ether, PPG-3 decyl ether, PPG-4 decyl ether, PPG-5 decyl ether, PPG-6 decyl ether, PPG-7 decyl ether, PPG-2 octyl ether, PPG-3 octyl ether, PPG-4 octyl ether, PPG-5 octyl ether, PPG-6 octyl ether, PPG-7 octyl ether, PPG-8 octyl ether, PPG-2 hexyl ether, PPG-3 hexyl ether, PPG-4 hexyl ether, PPG-5 hexyl ether, PPG-6 hexyl ether, PPG-7 hexyl ether, PPG-8 hexyl ether, PPG-9 hexyl ether, PPG-4 butyl ether, PPG-5 butyl ether, PPG-6 butyl ether, PPG-7 butyl ether, PPG-8 butyl ether, PPG-9 butyl ether, PPG-10 butyl ether, PPG-11 butyl ether, PPG-12 butyl ether, PPG-13 butyl ether, and PPG-14 butyl ether (Ucon® Fluid AP) are particularly preferred.

It has been found that with a PPG addition product such as PPG-15 stearyl ether (Arlamol® E), it was not possible to achieve the same good release of perspiration-inhibiting active substance compared to addition products of 1 to 14 propylene oxide units with univalent or polyvalent $C_{3-16}$ alkanols.

PPG-3 myristyl ether and PPG-14 butyl ether are particularly preferred according to the present invention, with PPG-3 myristyl ether most preferable.

Combinations of di-n-octyl carbonate and PPG-3 myristyl ether, di-2-ethylhexyl carbonate and PPG-3 myristyl ether, di-n-octyl carbonate and PPG-14 butyl ether, and di-2-ethylhexyl carbonate and PPG-14 butyl ether are also preferred.

The at least one addition product of 1 to 14 propylene oxide units with univalent or polyvalent $C_{3-16}$ alkanols can be present in a quantity of from 1 to 5 wt %, preferably 2 to 4 wt %, more preferably 2.5 to 3 wt %, based on total emulsion.

Compositions particularly preferred according to the present invention contain oil components representing symmetrical, asymmetrical, or cyclic esters of carbonic acid with linear or branched $C_6$ to $C_{22}$ alkanols at a weight ratio of 4 to 19 with respect to oil components representing addition products of 1 to 14 propylene oxide units with univalent or polyvalent $C_{3-16}$ alkanols. This weight ratio is preferably 5 to 15, particularly preferably 6 to 14, and most preferably 7 to 13. The same good effects regarding release of the perspiration-inhibiting active substance were not achieved with a weight ratio below 2.

Compositions according to the present invention contain 0 to a maximum of 3 wt %, preferably 0 to a maximum of 2.5 wt %, particularly preferably 0 to a maximum of 2 wt %, and most preferably 0 to a maximum of 1 wt % cyclomethicone, based on total weight of emulsion.

Compositions according to the present invention furthermore contain 75 to 90 wt % dispersed aqueous phase having at least one perspiration-inhibiting active substance and at least one compound chosen from water-soluble polyvalent $C_2$ to $C_9$ alkanols having 2 to 6 hydroxyl groups, and water-soluble polyethylene glycols having 3 to 20 ethylene oxide units.

Aqueous phase concentration is preferably 78 to 88 wt %, particularly preferably 80 to 86 wt %, and most preferably 81 to 84 wt %, based on total weight of the emulsion.

Free water content is 0 to 50 wt %, preferably 5 to 40 wt %, particularly preferably 10 to 30 wt %, and most preferably 15 to 20 wt %, based on total weight of the emulsion. Bound water of crystallization, for example, from the perspiration-inhibiting active substances, is not considered to be free water.

Emulsifying constituents are not considered to be aqueous phase for purposes of this application.

The aqueous phase of compositions according to the present invention includes at least one perspiration-inhibiting active substance (also referred to as an antiperspirant active substance) chosen from water-soluble astringent inorganic and organic aluminum-zirconium compounds. Aluminum-zirconium compounds are notable for particularly high efficiency along with good skin compatibility. They impart to the aqueous phase a higher refractive index $n_D$ than zirconium-free aluminum compounds. Particularly preferred antiperspirant active substances are selected from aluminum-zirconium glycol complexes (e.g., aluminum-zirconium propylene glycol complexes); aluminum-zirconium chlorohydrates such as aluminum-zirconium trichlorohydrate, aluminum-zirconium tetrachlorohydrate, aluminum-zirconium pentachlorohydrate, and aluminum-zirconium octachlorohydrate; and aluminum-zirconium chlorohydrate glycine complexes such as aluminum-zirconium trichlorohydrex glycine, aluminum-zirconium tetrachlorohydrex glycine, aluminum-zirconium pentachlorohydrex glycine, and aluminum-zirconium octachlorohydrex glycine. "Water solubility" according to the present invention refers to solubility of at least 5 wt % at 20° C. (i.e., quantities of at least 5 g of the antiperspirant active substance are soluble in 95 g water at 20° C.). Antiperspirant active substances can be used as an aqueous or glycolic solution or as an aqueous or glycolic solubilizate.

Particularly preferred compositions according to the present invention are characterized in that the at least one antiperspirant active substance is contained in the overall composition in a quantity from 3 to 27 wt %, by preference 5 to 22 wt %, and in particular 10 to 20 wt %, based on the total weight of the active substance (USP [U.S. Pharmacopoeia]). The quantity of perspiration-inhibiting salt(s) indicated in the present patent application in wt % is to be calculated according to the method of the U.S. Pharmacopoeia (USP), according to which bound water of crystallization and other ligands, e.g. glycine, are excluded.

Use of aluminum-zirconium tetrachlorohydrex glycine complexes (commercially available, for example, by Reheis under the designation Rezal® 36 G Rezal® 36 G C solution) may be particularly preferred according to the present invention.

The aqueous phase of compositions according to the present invention further include at least one compound chosen from water-soluble polyvalent $C_2$ to $C_9$ alkanols having 2 to 6 hydroxyl groups and water-soluble polyethylene glycols having 3 to 20 ethylene oxide units. Addition of these compounds aides in achieving transparency of the entire emulsion. Without these polyols, the refractive index of the aqueous phase would be too low to be capable of being adapted to the refractive index of the oil phase. These water-soluble polyol components furthermore contribute to stability of the emulsion.

Water-soluble polyol components preferably include 1,2-propylene glycol, 1,3-propylene glycol, 2-methyl-1,3-propanediol, glycerol, butylene glycols such as preferably 1,2-butylene glycol, particularly preferably 1,3-butylene glycol, and 1,4-butylene glycol, pentylene glycols such as 1,2-pentanediol and 1,5-pentanediol, hexanediols such as 1,2-hexanediol and 1,6-hexanediol, hexanetriols such as 1,2,6-hexanetriol, 1,2-octanediol, 1,8-octanediol, dipropylene glycol, tripropylene glycol, diglycerol, triglycerol, and mixtures of the aforesaid substances. Preferred water-soluble polyethylene glycols include PEG-3, PEG-4, PEG-6, PEG-7, PEG-8, PEG-9, PEG-10, PEG-12, PEG-14, PEG-16, PEG-18, and PEG-20, as well as mixtures thereof, with PEG-3 to PEG-8 being particularly preferred. Sugars, sugar alcohols, and certain sugar derivatives such as erythritol, sorbitol, xylitol, fructose, glucose, maltose, maltitol, mannitol, inositol, sucrose, trehalose, and xylose can also be used according to the present invention; however, because of their tackiness, they are less suitable or are suitable only in small quantities.

1,2-Propylene glycol, 1,3-butylene glycol, dipropylene glycol, and 1,2-hexanediol, as well as mixtures thereof, are preferred. Preferred polyol mixtures contain 1,2-propylene glycol and dipropylene glycol. Particularly preferred polyol mixtures contain 1,2-propylene glycol and dipropylene glycol at a weight ratio from 4:1 to 2:1. These mixtures exhibit particularly balanced properties with regard to transparency, active-substance release, skin feel, and skin compatibility.

Preferred compositions according to the present invention contain the at least one compound chosen from water-soluble polyvalent $C_2$ to $C_9$ alkanols having 2 to 6 hydroxyl groups, and water-soluble polyethylene glycols having 3 to 20 ethylene oxide units in an amount of from 20 to 60 wt %, preferably 25 to 55 wt %, particularly preferably 30 to 50 wt %, most preferably 35 to 45 wt %, based on total weight of the emulsion.

Compositions according to the present invention furthermore include at least one silicone-based water-in-oil emulsifier having at least one alkyl substituent R having 4 to 20 carbon atoms.

Water-in-oil emulsifiers that are particularly preferred are poly-($C_2$-$C_3$)alkylene glycol-modified silicones that are hydrophobically modified with $C_4$-$C_{20}$ alkyl groups. The hydrophobic alkyl substituent R having 4 to 20 carbon atoms is preferably chosen from n-butyl, n-pentyl, n-hexyl, n-heptyl, n-octyl, 2-ethylhexyl, n-decyl, n-undecyl, n-dodecyl, n-tetradecyl, n-hexadecyl=cetyl, n-octadecyl=stearyl, and n-eicosanyl=arachyl. Cetyl substituents are most preferred.

Particularly preferred silicone-based water-in-oil emulsions include Cetyl PEG/PPG-10/1 Dimethicone (formerly Cetyl Dimethicone Copolyol, obtainable as Abil EM 90), also preferably Cetyl PEG/PPG-7/3 Dimethicone, PEG/PPG-10/3 Oleyl Ether Dimethicone, Lauryl Dimethicone PEG-15 Crosspolymer, Cetyl PEG/PPG-15/15 Butyl Ether Dimethicone, Alkyl Methicone Copolyols, and Alkyl Dimethicone Ethoxy Glucoside. Cetyl PEG/PPG-10/1 Dimethicone is most preferred.

In addition to the hydrophobically alkyl-modified silicone-based water-in-oil emulsifiers listed above, in a preferred embodiment of the invention the silicone-based water-in-oil emulsifiers include those whose previous INCI name was Dimethicone Copolyol, having the current INCI names PEG-x Dimethicone (where x=2 to 20, preferably 3 to 17, particularly preferably 11 to 12), PEG/PPG a/b Dimethicone (where a and b, mutually independently, are numbers from 2 to 30, preferably 3 to 30, and particularly preferably 12 to 20, in particular 14 to 18), Bis-PEG/PPG-c/d Dimethicone (where c and d, mutually independently, are numbers from 10 to 25, preferably 14 to 20, and particularly preferably 14 to 16), and Bis-PEG/PPG-e/f PEG/PPG g/h Dimethicone (where e, f, g, and h, mutually independently, are numbers from 10 to 20, preferably 14 to 18, and particularly preferably 16). PEG/PPG-18/18 dimethicone, commercially available in a 1:9 mixture with cyclomethicone as DC 3225 C or DC 5225 C, PEG/PPG-4/12 Dimethicone, commercially available under the name Abil B 8852, and Bis-PEG/PPG-14/14 Dimethicone, commercially available in a mixture with cyclomethicone as Abil EM 97 (Goldschmidt), Bis-PEG/PPG-20/20 Dimethicone, commercially available under the name Abil B 8832, PEG/PPG-5/3 Trisiloxane (Silsoft 305), and PEG/PPG-20/23 Dimethicone (Silsoft 430 and Silsoft 440), are particularly preferred.

Preferred compositions according to the present invention contain the at least one silicone-based water-in-oil emulsifier having at least one alkyl substituent R having 4 to 20 carbon atoms in an amount from 1 to 4 wt %, preferably 1.5 to 3.5 wt %, particularly preferably 2 to 3 wt %, extraordinarily preferably 2.2 to 2.5 wt %, based on total weight of the emulsion.

Compositions according to the present invention are stable even without silicone-free water-in-oil emulsifiers, and therefore can be free of them. It has been found that certain silicone-free water-in-oil emulsifiers can negatively influence the active-substance release of the compositions according to the present invention.

Examples of such silicone-free W/O emulsifiers excluded according to the present invention are chosen from substances of the general formula A-O—$(CHR^1$—X—$CHR^2$—O-$)_a$-A', where A and A' represent identical or different hydrophobic organic residues, a represents a number from 1 to 100, by preference 2 to 60, in particular 5 to 40, X represents a single bond or the group —$CHOR^3$, $R^1$ and $R^2$ represent a hydrogen atom or a methyl group, and are selected so that the two residues do not simultaneously represent methyl, and $R^3$ represents a hydrogen atom or a branched or unbranched, saturated or unsaturated alkyl or acyl group having 1 to 20 carbon atoms.

Further excluded silicone-free W/O emulsifiers are chosen so that the residues A and A' are selected from the group of branched and unbranched, saturated and unsaturated alkyl and acyl residues and hydroxyacyl residues having 10 to 30 carbon atoms, and further from the hydroxyacyl groups connected to one another via ester functions according to the pattern: OOC—R"—CR'H—(OOC—R"—CR'H)$_b$—OOC—R"—CHR', where R' is a branched and unbranched alkyl group having 1 to 20 carbon atoms, R" is a branched and unbranched alkylene groups having 1 to 20 carbon atoms, and b is a value of 0 to 200.

Further excluded silicone-free W/O emulsifiers are chosen from
(1) saturated alcohols having 8 to 24 carbon atoms, in particular having 16 to 22 carbon atoms (e.g., cetyl alcohol, stearyl alcohol, arachidyl alcohol, or behenyl alcohol, or mixtures of said alcohols), such as those obtained from industrial hydrogenation of vegetable and animal fatty acids;
(2) ethoxylated alcohols and carboxylic acids having 8 to 24 carbon atoms, in particular having 16 to 22 carbon atoms, that have an HLB value from 1 to 8 (e.g., Laureth-1 or Laureth-4);
(3) partial esters of a polyol having 3 to 6 carbon atoms with saturated and/or unsaturated, branched and/or unbranched fatty acids having 8 to 24, in particular 12 to 18 carbon atoms. Such partial esters include the monoglycerides of palmitic, stearic, and oleic acid, the sorbitan mono- and/or diesters, in particular those of myristic acid, palmitic acid, stearic acid, or of mixtures of said fatty acids. Also to be mentioned here are the methyl esters of trimethylolpropane, erythritol, or pentaerythritol with saturated fatty acids having 14 to 22 carbon atoms. Also usable are the industrial monoesters obtained by esterification of 1 mol polyol with 1 mol fatty acid, and a mixture of monoesters, diesters, triesters, and optionally unesterified polyol.
(4) polyglycerol esters of saturated and/or unsaturated, branched and/or unbranched alkanecarboxylic acids having a chain length from 8 to 24, in particular 12 to 18 carbon atoms, having up to 10 glycerol units, by preference up to 3 glycerol units, and a degree of esterification from 1 to 10, by preference 1 to 5;
(5) mono- and/or polyglycerol ethers of saturated and/or unsaturated, branched and/or unbranched alcohols having a chain length from 8 to 30, in particular 12 to 18 carbon atoms, having up to 10 glycerol units, by preference up to 3 glycerol units, and a degree of etherification from 1 to 10, by preference from 1 to 5;
(6) propylene glycol esters of saturated and/or unsaturated, branched and/or unbranched alkanecarboxylic acids having a chain length from 8 to 24, in particular 12 to 18 carbon atoms;
(7) methyl glucose esters of saturated and/or unsaturated, branched and/or unbranched alkanecarboxylic acids having a chain length from 8 to 24, in particular 12 to 18 carbon atoms;
(8) polyglycerol-methyl glucose esters of saturated and/or unsaturated, branched and/or unbranched alkanecarboxylic acids having a chain length from 8 to 24, in particular 12 to 18 carbon atoms.

Further examples of silicone-free W/O emulsifiers excluded according to the present invention are glyceryl lanolate, glyceryl monostearate, glyceryl distearate, glyceryl monoisostearate, glyceryl monomyristate, glyceryl monooleate, diglyceryl monostearate, glyceryl monolaurate, glyceryl monocaprinate, glyceryl monocaprylate, diglyceryl monoisostearate, diglyceryl diisostearate, propylene glycol monostearate, propylene glycol monolaurate, sorbitan monoisostearate, sorbitan monolaurate, sorbitan monocaprylate, sorbitan sesquistearate, sorbitan monoisooleate, sucrose distearate, cetyl alcohol, stearyl alcohol, arachidyl alcohol, behenyl alcohol, isobehenyl alcohol, 2-ethylhexylglycerol ether, selachyl alcohol, chimyl alcohol, polyethylene glycol (2)stearyl ether(Steareth-2), glyceryl sorbitan stearate, polyglyceryl-4 isostearate, polyglyceryl-2 sesquiisostearate, PEG-7 hydrogenated castor oil, isostearyldiglyceryl succinate, PEG-5 cholesteryl ether, PEG-30 dipolyhydroxystearate, decaglyceryl heptaoleate, polyglyceryl-3 diisostearate, PEG-8 distearate, diglycerol dipolyhydroxystearate, glycerol isostearate, sorbitan isostearate, polyglyceryl-3 methyl glucose distearate, PEG-2 stearate, PEG-45/dodecyl glycol copolymer, PEG-22/dodecyl glycol copolymer, and methoxy PEG-22/dodecyl glycol copolymer.

Compositions according to the present invention further contain at least one polyethylene glycol ether of a linear or branched C12 to C22 alkanol with 20 to 150 ethylene oxide units. These compounds are known as oil-in-water emulsifiers.

It has been surprisingly found that the addition of such polyethylene glycol ethers of a linear or branched $C_{12}$ to $C_{22}$ alkanol with 20 to 150 ethylene oxide units greatly improves active-substance release of the perspiration-inhibiting active substance. It was particularly surprising that not all oil-in-water emulsifiers exert this promoting effect on compositions according to the present invention, not even those falling within the same HLB value range as the polyethylene glycol ethers, preferred according to the present invention, of a linear or branched $C_{12}$ to $C_{22}$ alkanol with 20 to 150 ethylene oxide units.

Preferred compositions according to the present invention include at least one polyethylene glycol ether of a linear or branched $C_{12}$ to $C_{22}$ alkanol with 20 to 150 ethylene oxide units chosen from Laureth-20, Laureth-25, Laureth-30, Laureth-35, Laureth-40, Laureth-45, Laureth-50, Laureth-55, Laureth-60, Laureth-65, Laureth-70, Laureth-75, Laureth-80, Laureth-85, Laureth-90, Laureth-95, Laureth-100, Myristeth-20, Myristeth-25, Myristeth-30, Myristeth-35, Myristeth-40, Myristeth-45, Myristeth-50, Myristeth-55, Myristeth-60, Myristeth-65, Myristeth-70, Myristeth-75, Myristeth-80, Myristeth-85, Myristeth-90, Myristeth-95, Myristeth-100, Ceteth-20, Ceteth-25, Ceteth-30, Ceteth-35, Ceteth-40, Ceteth-45, Ceteth-50, Ceteth-55, Ceteth-60, Ceteth-65, Ceteth-70, Ceteth-75, Ceteth-80, Ceteth-85, Ceteth-90, Ceteth-95, Ceteth-100, Ceteth-110, Ceteth-120, Ceteth-130, Ceteth-140, Ceteth-150, Isoceteth-20, Isoceteth-25, Isoceteth-30, Isoceteth-35, Isoceteth-40, Isoceteth-45, Isoceteth-50, Isoceteth-55, Isoceteth-60, Isoceteth-65, Isoceteth-70, Isoceteth-75, Isoceteth-80, Isoceteth-85, Isoceteth-90, Isoceteth-95, Isoceteth-100, Isoceteth-110, Isoceteth-120, Isoceteth-130, Isoceteth-140, Isoceteth-150, Steareth-20, Steareth-25, Steareth-30, Steareth-35, Steareth-40, Steareth-45, Steareth-50, Steareth-55, Steareth-60, Steareth-65, Steareth-70, Steareth-75, Steareth-80, Steareth-85, Steareth-90, Steareth-95, Steareth-100, Steareth-110, Steareth-120, Steareth-130, Steareth-140, Steareth-150, Isosteareth-20, Isosteareth-25, Isosteareth-30, Isosteareth-35, Isosteareth-40, Isosteareth-45, Isosteareth-50, Isosteareth-55, Isosteareth-60, Isosteareth-65, Isosteareth-70, Isosteareth-75, Isosteareth-80, Isosteareth-85, Isosteareth-90, Isosteareth-95, Isosteareth-100, Isosteareth-110, Isosteareth-120, Isosteareth-130, Isosteareth-140, Isosteareth-150, Arachideth-20, Arachideth-25, Arachideth-30, Arachideth-35, Arachideth-40, Arachideth-45, Arachideth-50, Arachideth-55, Arachideth-60, Arachideth-65, Arachideth-70, Arachideth-75, Arachideth-80, Arachideth-85, Arachideth-90, Arachideth-95, Arachideth-100, Arachideth-110, Arachideth-120, Arachideth-130, Arachideth-140, Arachideth-150, Beheneth-20, Beheneth-25, Beheneth-30, Beheneth-35, Beheneth-40, Beheneth-45, Beheneth-50, Beheneth-55, Beheneth-60, Beheneth-65, Beheneth-70, Beheneth-75, Beheneth-80, Beheneth-85, Beheneth-90, Beheneth-95, Beheneth-100, Beheneth-110, Beheneth-120, Beheneth-130, Beheneth-140, Beheneth-150, and mixtures thereof. Steareth-100 is extraordinarily preferred.

Preferred compositions according to the present invention include at least one polyethylene glycol ether of a linear or branched $C_{12}$ to $C_{22}$ alkanol with 20 to 150 ethylene oxide units in an amount of from 1 to 4 wt %, preferably 1.5 to 3.5, particularly preferably 2 to 3 wt %, most preferably 2.2 to 2.6 wt %, based on total weight of the emulsion.

Further preferred compositions according to the present invention include Steareth-100 in an amount of from 1 to 4 wt %, preferably 1.5 to 3.5, particularly preferably 2 to 3 wt %, extraordinarily preferably 2.2 to 2.6 wt %, based on total weight of the emulsion.

Further preferred compositions according to the present invention include 1 to 10 wt %, preferably 2 to 8 wt %, particularly preferably 3 to 7 wt %, most preferably 4 to 6 wt % ethanol, based on total weight of the emulsion. Ethanol content of this kind advantageously assists emulsion stability and transparency.

Viscosity indications refer to measurements with a rotary viscometer from the Brookfield company, selecting the spindle and rotation speed recommended in the Brookfield company manual "More Solutions to Sticky Problems."

Using T-bar spindles and a Helipath

TABLE VIS-1

Brookfield model LV and HA viscometers; upper limit of optimum viscosity range for measurement with measurement parameters indicated (in mPas [milliPascal × second])

| Unit | Shear rate (revolutions per minute, rpm) | Spindle | | | |
|---|---|---|---|---|---|
| | | T-A | T-B | T-C | T-D |
| LVT | 0.3 | 66,600 | 133,000 | 333,000 | 666,000 |
| LVT | 0.6 | 33,300 | 66,600 | 166,000 | 333,000 |
| LVT | 1.5 | 13,300 | 26,600 | 133,000 | 333,000 |
| LVT | 3 | 6,660 | 13,300 | 33,300 | 66,600 |
| LVT | 6 | 3,330 | 6,660 | 16,600 | 33,300 |
| LVF | | | | | |
| LVT | 12 | 1,660 | 3,330 | 8,300 | 16,600 |
| LVF | | | | | |
| HAT | 0.5 | 800,000 | 1,600,000 | 4,000,000 | 8,000,000 |
| HAT | 1 | 400,000 | 800,000 | 2,000,000 | 4,000,000 |
| HAF | | | | | |
| HAF | 2 | 200,000 | 400,000 | 1,000,000 | 2,000,000 |
| HAT | 2.5 | 160,000 | 320,000 | 800,000 | 1,000,000 |
| HAT | 5 | 80,000 | 160,000 | 400,000 | 800,000 |
| HAF | | | | | |

TABLE VIS-2

Brookfield model RV viscometer; upper limit of optimum viscosity range for measurement with measurement parameters indicated (in mPas [milliPascal × second])

| Unit | Shear rate (revolutions per minute, rpm) | Spindle | | | |
|---|---|---|---|---|---|
| | | T-A | T-B | T-C | T-D |
| RVT | 0.5 | 400,000 | 800,000 | 2,000,000 | 4,000,000 |
| RVT | 1.0 | 200,000 | 400,000 | 1,000,000 | 2,000,000 |
| RVT | 2.0 | 100,000 | 200,000 | 500,000 | 1,000,000 |
| RVF | 2.5 | 80,000 | 150,000 | 400,000 | 800,000 |
| RVF | 4 | 50,000 | 100,000 | 250,000 | 500,000 |
| RVT | 5 | 40,000 | 80,000 | 200,000 | 400,000 |

The viscosity indicated represents the upper limit value for the optimum measurement range for the respective spindle/rotation speed combination. If two different measurement parameter combinations are possible for a viscosity range, the spindle/rotation speed combination furnishing the higher scale value is selected. Viscosity indications furthermore refer to the composition 24 hours after manufacture and at a temperature of 21° C., measured with a Helipath.

Compositions preferred according to the present invention, having a preferred viscosity, are particularly well suited for application with a ball applicator or from a gel dispenser. In order to illustrate transparency of the composition to the consumer, a transparent package is preferred.

Compositions preferred according to the present invention can further contain additives such as deodorant active substances, preferably 2-ethylhexylglycerol ether (Sensiva SC 50), UV filters, antioxidants, desensitizing active substances such as amino acids, proteins, and protein hydrolysates, vitamins and vitamin precursors, in particular panthenol, preservatives, and antibacterial active substances.

The examples below are intended to illustrate the invention without limiting it thereto.

| Transparent perspiration-inhibiting W/O emulsion gel - | |
|---|---|
| Diethylhexyl carbonate | 12 wt % |
| Cetyl PEG/PPG-10/1 dimethicone | 2 wt % |
| PPG-3 myristyl ether | 2 wt % |
| Ethanol (96%) | 5 wt % |
| Perfume oil | 0.6 wt % |
| Aluminum-zirconium tetrachlorohydrex glycine | 21 wt % |
| 1,2-Propylene glycol | 24.4 wt % |
| Dipropylene glycol | 13.4 wt % |
| Steareth-100 | 2 wt % |
| Water | 17.6 wt % |

This transparent perspiration-inhibiting W/O emulsion was applied from a transparent gel dispenser onto the skin in the underarm area. A long-lasting perspiration-inhibiting effect was observed.

We claim:

1. Transparent perspiration-inhibiting composition in the form of a water-in-oil emulsion, comprising:
   a) an external oil phase in an amount of 10 to 20 wt % and having
   a.i) at least one symmetrical, asymmetrical, or cyclic ester of carbonic acid with linear or branched C6 to C22 alkanols,
   a.ii) at least one addition product of 1 to 14 propylene oxide units with univalent or polyvalent C3-16 alkanols, and
   a.iii) 0 to a maximum of 3 wt % cyclomethicone,
   b) a dispersed aqueous phase in an amount of 75 to 90 wt % and having at least one perspiration-inhibiting active substance chosen from aluminum-zirconium compounds, and at least one compound chosen from water-soluble polyvalent Ca to C9 alkanols having 2 to 6 hydroxyl groups and water-soluble polyethylene glycols having 3 to 20 ethylene oxide units, wherein the water-soluble polyvalent C2 to C9 alkanols having 2 to 6 hydroxyl groups and water-soluble polyethylene glycols having 3 to 20 ethylene oxide units are present in an amount of 20 to 60 wt. %,
   c) at least one silicone-based water-in-oil emulsifier having at least one alkyl substituent R having 4 to 20 carbon atoms present in an amount of 2 to 3 wt. %,
   d) at least one polyethylene glycol ether of a linear or branched C12 to C22 alkanol with 35 to 150 ethylene oxide units present in an amount of 2 to 3 wt. % and selected from the group consisting of Laureth-35, Laureth-40, Laureth-45, Laureth-50, Laureth-55, Laureth-60, Laureth-65, Laureth-70, Laureth-75, Laureth-80, Laureth-85, Laureth-90, Laureth-95, Laureth-100, Myristeth-35, Myristeth-40, Myristeth-45, Myristeth-50, Myristeth-55, Myristeth-60, Myristeth-65, Myristeth-70, Myristeth-75, Myristeth-80, Myristeth-85, Myristeth-90, Myristeth-95, Myristeth-100, Ceteth-35, Ceteth-40, Ceteth-45, Ceteth-50, Ceteth-55, Ceteth-60, Ceteth-65, Ceteth-70, Ceteth-75, Ceteth-80, Ceteth-85, Ceteth-90, Ceteth-95, Ceteth-100, Ceteth-110, Ceteth-120, Ceteth-130, Ceteth-140, Ceteth-150, Isoceteth-35, Isoceteth-40, Isoceteth-45, Isoceteth-50, Isoceteth-55, Isoceteth-60, Isoceteth-65, Isoceteth-70, Isoceteth-75, Isoceteth-80, Isoceteth-85, Isoceteth-90, Isoceteth-95, Isoceteth-100, Isoceteth-110, Isoceteth-120, Isoceteth-130, Isoceteth-140, Isoceteth-150, Steareth-35, Steareth-40, Steareth-45, Steareth-50, Steareth-55, Steareth-60, Steareth-65, Steareth-70, Steareth-75, Steareth-80, Steareth-85, Steareth-90, Steareth-95, Steareth-100, Steareth-110, Steareth-120, Steareth-130, Steareth-140, Steareth-150, Isosteareth-35, Isosteareth-40, Isosteareth-45, Isosteareth-50, Isosteareth-55, Isosteareth-60, Isosteareth-65, Isosteareth-70, Isosteareth-75, Isosteareth-80, Isosteareth-85, Isosteareth-90, Isosteareth-95, Isosteareth-100, Isosteareth-110, Isosteareth-120, Isosteareth-130, Isosteareth-140, Isosteareth-150, Arachideth-35, Arachideth-40, Arachideth-45, Arachideth-50, Arachideth-55, Arachideth-60, Arachideth-65, Arachideth-70, Arachideth-75, Arachideth-80, Araehideth-85, Arachideth-90, Arachideth-95, Arachideth-100, Arachideth-110, Arachideth-120, Arachideth-130, Arachideth-140, Arachideth-150, Beheneth-35, Beheneth-40, Beheneth-45, Beheneth-50, Beheneth-55, Beheneth-60, Beheneth-65, Beheneth-70, Beheneth-75, Beheneth-80, Beheneth-85, Beheneth-90, Beheneth-95, Beheneth-100, Beheneth-110, Beheneth-120, Beheneth-130, Beheneth-140, Beheneth-150, and mixtures thereof,
   e) no silicone-free water-in-oil emulsifier,
   all wt % referring to total weight of the emulsion;
   wherein the at least one perspiration-inhibiting active substance is present in an amount of from 10 to 22 wt %, based on active-substance content per total weight of the emulsion and wherein the composition has a viscosity of from 30,000 to 150,000 mPas at 21° C.

2. Composition according to claim 1, wherein oil components a.i) and a.ii) are present at a weight ratio from 4 to 19.

3. Composition according to claim 1 further comprising 1 to 10 wt % ethanol, based on total weight of the emulsion.

4. Composition according to claim 1, wherein the at least one polyethylene glycol ether is Steareth-100.

* * * * *